United States Patent [19]
Waisbren et al.

[11] 4,365,752
[45] Dec. 28, 1982

[54] WATER PULSATING UNIT FOR ORAL SYRINGE

[76] Inventors: Avery Waisbren, 5429 Santa Monica Blvd., Los Angeles, Calif. 90029; Arthur F. Kelson, 11701 Foster, Los Alamitos, Calif. 90720

[21] Appl. No.: 260,067

[22] Filed: May 4, 1981

[51] Int. Cl.³ .............................................. B05B 1/08
[52] U.S. Cl. ....................................... 239/381; 128/66
[58] Field of Search ................. 128/66; 239/102, 380, 239/381; 433/80; 366/119; 137/624.14

[56] References Cited

U.S. PATENT DOCUMENTS

| | | | |
|---|---|---|---|
| 2,727,509 | 12/1955 | Fortin | 128/66 |
| 3,067,739 | 12/1962 | Karlik | 128/66 |
| 3,278,165 | 10/1966 | Gaffney | 366/119 |
| 3,408,050 | 10/1968 | Jacobs | 366/119 |
| 3,687,369 | 8/1972 | Johnstone | 239/102 |
| 3,734,410 | 5/1973 | Bruno | 239/381 |
| 3,973,558 | 8/1976 | Stouffer et al. | 128/66 |
| 4,026,470 | 5/1977 | Crist | 239/102 |

Primary Examiner—Gene Mancene
Assistant Examiner—John J. Wilson
Attorney, Agent, or Firm—Roger A. Marrs

[57] ABSTRACT

A pulsating device is disclosed herein for interrupting the flow of water being discharged via a nozzle carried on a dental syringe. The device includes a body coupled between the syringe and the nozzle having a central cavity partially occupied by a flutter valve. The valve includes a broad, flat member pivotally carried at its mid-section in the cavity so as to interfere with a flow of water passing through the cavity from the syringe to the nozzle. One end of the member is weighted so that the member flutters across the ports of the syringe and the nozzle to interrupt the water flow in response to the incoming water pressure from the syringe.

1 Claim, 3 Drawing Figures

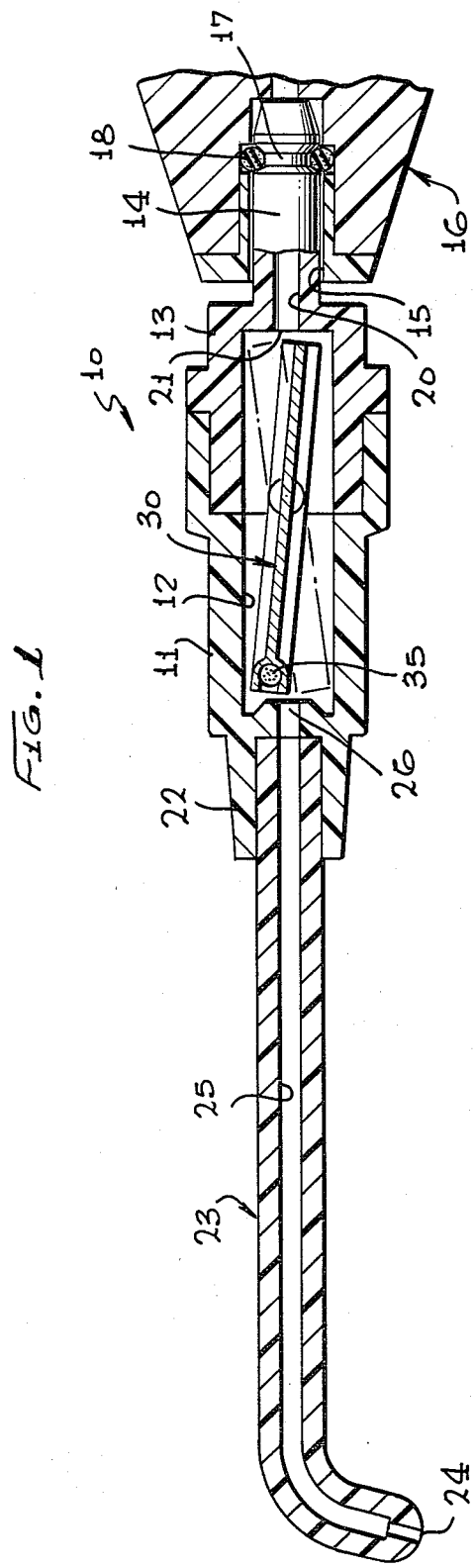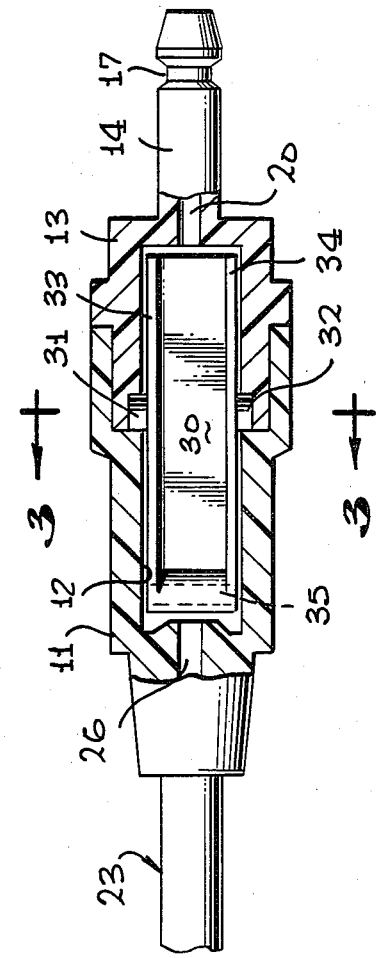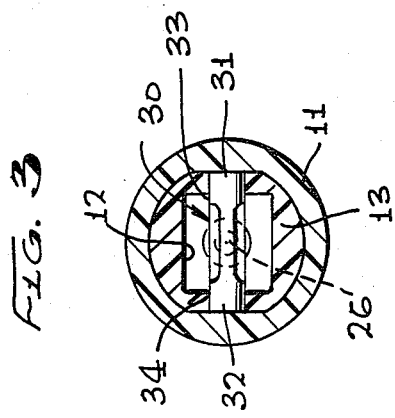

WATER PULSATING UNIT FOR ORAL SYRINGE

BACKGROUND OF THE INVENTION

1. Field of the Invention

The present invention relates to fluid oscillators capable of producing periodic pulsations in a fluid and, in particular, to a pulsating device adapted to be used with a dental syringe.

2. Brief Description of the Prior Art

Fluid oscillators have been developed which utilize fluid dynamic effects such as stream interaction and boundary layer control to provide a pulsating flow of fluid without any moving parts. In such practices, these devices generally must be constructed with fairly close tolerances in order to achieve satisfactory results, and the cost of such devices is generally quite high.

Still other oral hygiene appliances have been provided which deliver an intermittently pulse stream of water for dislodging foreign matter from the teeth and gum tissues and for the purpose of massaging gum tissue. All the current commercial oral hygiene units of this type operate in substantially the same manner. A liquid, usually water, is fed into an inlet chamber of a liquid pump from a liquid reservoir. The liquid pump is generally the reciprocating type which draws a quantity of liquid from the inlet chamber into the pump chamber on each intake stroke, and on each exhaust stroke delivers a quantity of liquid directly into a delivery tube which is connected to a removable jet nozzle. A separate discharge nozzle is provided for each family member who would use the appliance. These commercially available units usually further include a pulse intensity control that feeds back a portion of the pump liquid to the inlet chamber in order to reduce the pressure or force of the liquid discharged at the discharge end of the discharge nozzle. However, problems have been encountered with maintenance and repair of the pulsating unit since the unit is generally incorporated into the body of the appliance or syringe which is inaccessible for such purposes.

Previous attempts at providing suitable pulsating units or devices are shown in the disclosures of U.S. Pat. Nos. 3,499,440; 3,590,813 and 3,810,465. Although these prior devices have met with some success, difficulties have been encountered which are mentioned above.

Therefore, a long standing need has existed to provide a novel pulsating device which may be readily adapted for use with a variety of dental syringes for the purpose of pulsing the output stream of the syringe for various purposes including the irrigation, cleansing or massaging of biological tissue.

SUMMARY OF THE INVENTION

Accordingly, the above problems and dfficulties are obviated by the present invention which provides a novel pulsing device for use with a dental syringe which includes a body having a central cavity adapted to be positioned between the dental syringe and a discharge stem or nozzle whereby the pressurized water flow from the syringe is conducted via the body cavity to the discharge stem or nozzle via a flutter valve. The flutter valve is pivotally carried in the central cavity on the body at its mid-section. The valve includes a rod, flat member which is weighted at one end so that inertia of the weight will carry the member through its pivoting motion within the cavity. Pivoting of the member is in response to introduction of pressurized fluid such as water into the chamber or cavity from the syringe and maintaining movement of the opposite ends of the member with respect to the cavity's input and output ports effects interruption of the pressurized water stream discharging from the discharge stem or nozzle.

Therefore, it is among the primary objects of the present invention to provide a novel pulsating unit for a dental syringe which may be readily coupled between the discharge end of the syringe and the discharge stem or nozzle normally associated with the syringe so that the pressure discharge from the discharge nozzle is pulsed.

Another object of the present invention is to provide a novel pulsating unit which incorporates a flutter valve for readily interrupting the pressure fluid stream of a dental syringe so that the discharge from the nozzle is pulsating.

Another object of the present invention is to provide a novel pulsating unit for a dental syringe which is relatively inexpensive and employs a flutter valve operating in response to the discharge of a dental syringe for interrupting the main pressurized fluid stream so that a pulsating stream is produced.

Still a further object of the present invention is to provide a novel pulsating dental syringe whereby the normal main pressurized fluid stream is converted to a sequentially arranged series of liquid pulses by a flutter valve which is then discharged from a discharge stem or nozzle.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood by reference to the following description, taken in connection with the accompanying drawings, in which:

FIG. 1 is a longitudinal cross-sectional view of the novel pulsating device incorporating the present invention;

FIG. 2 is a sectional view of the pulsating device shown in FIG. 1; and

FIG. 3 is a transverse cross-sectional view of the pulsating device as taken in the direction of arrows 3—3 of FIG. 2.

DESCRIPTION OF PREFERRED EMBODIMENT

Referring to FIG. 1, the novel pulsating device or unit of the present invention is illustrated in the general direction of arrow 10 which includes a body 11 having a central cavity formed therein as indicated by numeral 12. It is to be particularly noted that the body 11 includes a rear portion 13 which is formed with a projection 14 intended to be inserted into a receptacle 15 carried on the end of a conventional or typical dental syringe indicated in general by the numeral 16. As is the usual practice, the projection 14 includes a reduced portion 17 which is occupied by a conventional O ring seal 18. The rear portion 13 includes a passage way 20 connecting at one end with the output port of the dental syringe 16 and terminating at its opposite end in an inlet port 21 leading into one end of the cavity 12.

The forward end of the body 11 includes a support portion 22 for insertably receiving and mounting a discharge stem or nozzle 23. The opposite end of the nozzle 23 from its end supported in portion 22 terminates in a discharge or jet orifice 24. The stem or nozzle 23 includes an elongated passage way 25 which terminates at one end in the jet nozzle 24 and terminates at its opposite end in an outlet port 26 leading from the internal cavity or chamber 12 of body 11.

Therefore, it can be seen that a fluid conduit exists from the dental syringe 16 through passage way 20 and into the chamber 12 via input port 21 and from the cavity 12 to the jet nozzle 24 via outlet port 26 and passage way 25.

In order to pulsate the fluid discharge from the jet nozzle 24, a flutter valve is incorporated into the cavity or chamber 12 which interferes with the flow of pressurized fluid, such as water, there through and which somewhat restricts the openings of the input and output ports 21 and 26 respectively. The flutter valve includes an elongated broad, flat member 30 which is movably carried on the body 11 via pivots 31 and 32, shown more clearly in FIG. 2. The member 30 further includes side ribs 33 and 34 which project upwardly and downwardly beyond the thickness of the member 30. The end of the member 30 closest to outlet port 26 is provided with a weight 35 which, by its inertia, causes the member to pivot on pivots 31 and 32. The pivot positions are illustrated in solid and broken lines in FIG. 1 within the chamber 12.

It can be seen in more detail in FIG. 2 that the pivots 31 and 32 are received within holes or apertures provided in the body 11 and that the pivots are coaxial with respect to each other. The pivots are located at the approximate mid-section of member 30 between its opposite ends. However, the weighted end 35 will cause the member to pivot.

In actual practice, the pulsing device 10 may be added to any conventional dental syringe by merely inserting the projection 14 into the receptacle normally provided for receiving the discharge nozzle. Next, pressurized water is introduced through the dental syringe and the pressurized water is then conducted via passage way 20 to the chamber cavity 12 of the pulsing device. The input water under pressure strikes the valve member 30 and causes it to pivot. The weighted end 35 causes the member to return to its original position. Pivoting of member 30 is sequential and is repeated over and over as long as pressurized water is introduced to the chamber via inlet port 21. The pulse water will exit from the chamber through outlet port 26 and via passage way 25, to the jet orifice 24. It is also to be noted that the extreme ends of member 30 are in close proximity to the ports 21 and 26 respectively so that some interference is encountered. This interference is intentional and adds to the pivoting action caused by the pressurized water from the dental syringe. Because of the weighted end 35, either the under side or the top side of member 30 will be exposed to the oncoming pressurized water stream at any given moment. Once the stream impacts or impinges against the exposed surface, pivoting is produced and the water impact will be against the opposite side in the next sequence.

Thus, the main pressurized water stream from the dental syringe is interrupted sequentially and it is this interruption that causes pulsing at the discharge jet 24.

While particular embodiments of the present invention have been shown and described, it will be obvious to those skilled in the art that changes and modifications may be made without departing from this invention in its broader aspects, and therefore, the aim in the appended claims is to cover all such changes and modifications as fall within the true spirit and scope of this invention.

What is claimed is:

1. A device for producing a pulsating stream from a main stream of pressurized water comprising the combination of:
   a body having inlet and outlet ports on opposite sides of a central cavity;
   said inlet port adapted to be connected to a source of pressurized water and said outlet port arranged to carry a discharge nozzle;
   rotary valve means movably carried on said body within said body cavity for yieldably interfering with flow of pressurized water conducted from said inlet port to said outlet port whereby a sequential series of pulsating water discharges from said nozzle in response to oscillatory rotary movement of said valve means;
   said valve means is a flutter valve pivotally carried on said body within said cavity;
   said flutter valve comprises an elongated member having pivots outwardly projecting in a lateral direction approximately mid-way between its opposite ends;
   said flutter valve member has movable opposite ends terminating in equally close proximity to said inlet and said outlet ports respectively;
   a weight carried on said valve member end in close proximity to said outlet port;
   said valve member is pivoted in response to the main fluid stream pressure whereby the main fluid stream pressure alternately strikes against one side and then the other side of said valve member at its end opposite to said end carrying said weight; and
   said valve member further includes a pair of spaced apart ribs carried on the opposite sides thereof respectively.

* * * * *